United States Patent [19]

Diehr et al.

[11] Patent Number: 4,992,456

[45] Date of Patent: Feb. 12, 1991

[54] FUNGICIDAL 2,5-DISUBSTITUTED 1,3,4-THIADIAZOLES

[75] Inventors: Hans-Joachim Diehr, Wuppertal; Albrecht Marhold, Leverkusen; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 430,388

[22] Filed: Nov. 1, 1989

[30] Foreign Application Priority Data

Nov. 12, 1988 [DE] Fed. Rep. of Germany ....... 3838432

[51] Int. Cl.$^5$ .................... C07D 285/12; A01N 43/82
[52] U.S. Cl. .................... 514/363; 514/342; 544/238; 544/333; 546/148; 546/172; 546/271; 548/131; 548/142
[58] Field of Search ............... 548/142, 131; 514/363, 514/342; 544/333, 238; 546/271, 172, 148

[56] References Cited

U.S. PATENT DOCUMENTS 4,432,847  2/1984  Fields .................................. 548/142

FOREIGN PATENT DOCUMENTS 1695897  2/1972  Fed. Rep. of Germany ...... 548/142
1568552  5/1969  France ............................... 548/142
 748422  5/1956  United Kingdom ................ 514/363
1237436  6/1977  United Kingdom ................ 514/363

OTHER PUBLICATIONS

Pharmaceuticals, Photographic, p. 1 (Belgian Patents Report No. 50/68).
Rec. Trav. Chim. Pays-Bas 90, No. 2, 97–104 (1971).
Abstr. Papers, Am. Chem. Soc., 1965, No. 150, 138.
Heterocyclus, 20, 19–22, 1983.

*Primary Examiner*—Robert Gerstl
*Attorney, Agent, or Firm*—Sprung, Horn, Kramer & Woods

[57] ABSTRACT

Fungicidal 2,5-disubstituted 1,3,4-thiadiazoles of the formula

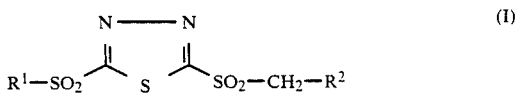

in which
  $R^1$ represents alkyl or unsubstituted or substituted aralkyl and
  $R^2$ represents in each case unsubstituted or substituted aryl or aralkyl, or represents an unsubstituted or substituted and optionally benzo-fused heterocyclic radical, excluding the compound 2,5-bis[(phenylmethyl)-sulphonyl]-1,3,4-thiadiazole.

11 Claims, No Drawings

FUNGICIDAL 2,5-DISUBSTITUTED 1,3,4-THIADIAZOLES

The present invention relates to new 2,5-disubstituted 1,3,4-thiadiazole derivatives, a process for their preparation and their use in agents for combating pests, above all as fungicides.

It is already known that certain 1,3,4-thiadiazoles, such as, for example, 2,5-bisalkylsulphonyl-1,3,4-thiadiazoles, have fungicidal properties (compare Belgian Patent No. 716,257).

The fungicidal action, inter alia, of 2-methylsulphonyl5-thiocyanomethylsulphonyl-1,3,4-thiadiazole is also known (compare Rec. Trav. Chim. Pays-Bas 90, No. 2, 97–104 (1971)).

However, the action of these compounds is not always completely satisfactory in all areas of use, especially when low amounts and concentrations are applied.

2,5-Dimethylsulphonyl-1,3,4-thiadiazole is also described as the starting compound for corresponding sulphonamides (compare Abstr. Papers, Am. Chem. Soc. 1965, No. 150, 138).

The compound 2,5-bis[(phenylmethyl)-sulphonyl]-1,3,4-thiadiazole is moreover known (compare Heterocyclus, 20, 19–22, 1983).

New 2,5-disubstituted 1,3,4-thiadiazole derivatives of the formula (I)

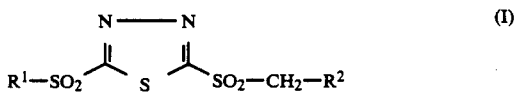

in which
- $R^1$ represents alkyl or unsubstituted or substituted aralkyl and
- $R^2$ represents in each case unsubstituted or substituted aryl or aralkyl, or represents an unsubstituted or substituted and/or optionally benzo-fused heterocyclic radical, excluding the compound 2,5-bis-[(phenylmethyl)-sulphonyl]-1,3,4-thiadiazole (compare Heterocyclus, 20, 19–22, 1983), have been found.

It has furthermore been found that the new 2,5-disubstituted 1,3,4-thiadiazole derivatives of the formula (I)

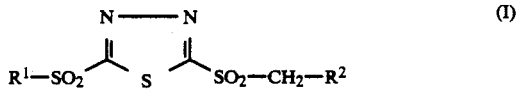

in which
- $R^1$ represents alkyl or unsubstituted or substituted aralkyl and
- $R^2$ represents in each case unsubstituted or substituted aryl or aralkyl, or represents an unsubstituted or substituted and/or optionally benzo-fused heterocyclic radical, are obtained by a process in which 2,5-dimercapto-1,3,4-thiadiazole derivatives of the formula (II)

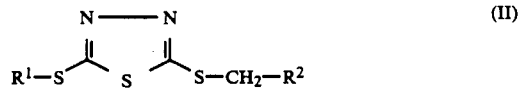

in which
- $R^1$ and $R^2$ have the abovementioned meanings, are reacted with an oxidizing agent, if appropriate in the presence of a diluent and if appropriate in the presence of a catalyst.

The 2,5-disubstituted 1,3,4-thiadiazole derivatives according to the invention exhibit a very good fungicidal activity and thus represent a valuable enrichment of the art.

In the general formulae, alkyl in general denotes straight-chain or branched alkyl having 1 to 8 carbon atoms, preferably having 1 to 6 and particularly preferably having 1 to 4 carbon atoms; examples which may be mentioned are methyl, ethyl, n- and i-propyl, n-, i-, sec.- and t-butyl, pentyl, hexyl and octyl.

Aryl in general as such or in combinations, such as aralkyl, in general represents an aromatic radical having 6 to 10 carbon atoms. Aryl radicals are preferably phenyl or naphthyl, and especially preferably phenyl.

Aralkyl in general represents in the aryl part having 6 to 10 and in the alkyl part having 1 to 6, preferably 1 to 5 carbon atoms in the definition of $R^1$ and 1 to 4 carbon atoms in the definition of $R^2$, particularly preferably having 1 to 3 or 1 or 2 carbon atoms in the alkyl part. Examples which may be mentioned are phenylmethyl, phenethyl, naphthylmethyl and naphthylethyl.

A heteroaromatic ring in general represents a 5- or 6-membered ring which contains one or more hetero atoms, preferably 1 to 3 identical or different hetero atoms, and the corresponding benzo-fused rings.

Preferred hetero atoms which may be mentioned are oxygen, sulphur and nitrogen; examples which may be mentioned are: pyridyl, pyrimidyl, pyridazyl, thienyl, furyl, pyrazolyl, thiadiazolyl, quinolyl, isoquinolyl, benzoxazolyl, benzothiazolyl, benzimidazolyl and 1,2,4-oxadiazolyl.

The substituents for the aryl radicals as such or in combinations, such as aralkyl and for the heterocyclic rings have the meanings given below.

Halogen in general as a substituent of the radicals represents fluorine, chlorine, bromine or iodine, preferably fluorine, chlorine or bromine, particularly preferably fluorine or chlorine.

Alkyl in general as a substituent of the radicals represents straight-chain or branched alkyl, preferably having 1 to 6, particularly preferably having 1 to 4, carbon atoms, and methyl, ethyl and t-butyl are especially preferred. The list of examples corresponds to that given above.

Alkoxy in general as a substituent of the radicals represents straight-chain or branched alkoxy having 1 to 6, particularly preferably 1 to 3, carbon atoms; examples which may be mentioned are: methoxy, ethoxy, n- and i-propoxy, n-, i-, sec.- and t-butoxy, n-hexoxy and i-hexoxy.

Alkylsulphonyl in general as a substituent of the radicals represents straight-chain or branched alkylsulphonyl having 1 to 4, particularly preferably having 1 to 3, carbon atoms, especially preferably having 1 carbon atom; examples which may be mentioned are: methylsulphonyl, ethylsulphonyl and n-, i-, sec.- and t-butylsulphonyl.

Halogenoalkyl, halogenoalkoxy and halogenoalkylsulphonyl in general as substituents in the radicals represent straight-chain or branched radicals having in each case 1 to 4 carbon atoms, particularly preferably having 1 or 2 carbon atoms, and in each case 1 to 5 identical or different halogen atoms as defined under halogen; examples which may be mentioned are: fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chloro- difluoro-methyl, trifluorochloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy, trifluorochloroethoxy and fluoromethylsulphonyl, chloromethylsulphonyl, bromoethylsulphonyl, fluoroethylsulphonyl, chloroethylsulphonyl, bromomethylsulphonyl, fluoropropylsulphonyl, chloropropylsulphonyl, bromopropylsulphonyl, fluorobutylsulphonyl, chlorobutylsulphonyl, fluoro-isopropylsulphonyl, chloro-isopropylsulphonyl, chlorobutylsulphonyl, difluoromethylsulphonyl, trifluoromethylsulphonyl, dichloromethylsulphonyl, trichloromethylsulphonyl, difluoroethylsulphonyl, trifluoroethylsulphonyl, tetrafluoroethylsulphonyl, trichloroethylsulphonyl, chlorodifluoromethylsulphonyl and trifluorochloroethylsulphonyl, and trifluoromethyl, trifluoromethoxy and trifluoromethylsulphonyl are to be singled out in particular.

Alkoxycarbonyl in general as a substituent in the radicals represents straight-chain or branched alkoxycarbonyl having 1 to 4, preferably 1 or 2, carbon atoms in the alkoxy radical; examples which may be mentioned are: methoxycarbonyl, ethoxycarbonyl, n-propoxycarbonyl, i-propoxycarbonyl and n-, i-, sec.- and t-butoxycarbonyl.

Substitution by one or more substituents means substitution by 1 to 5, particularly preferably 1 to 3 or 1 or 2 substituents, unless stated otherwise.

Formula (I) provides a general definition of the 2,5disubstituted 1,3,4-thiadiazole derivatives according to the invention. Preferred compounds of the formula (I) are those in which $R^1$ represents straight-chain or branched alkyl having 1 to 6 carbon atoms or aralkyl which has 1 to 5 carbon atoms in the alkyl part and 6 to 10 carbon atoms in the aryl part and is unsubstituted or substituted by one or more identical or different substituents, possible substituents on the aryl being: halogen, nitro, cyano, alkyl and alkoxy having in each case 1 to 6 carbon atoms and halogenoalkyl, halogenoalkoxy, alkylsulphonyl, halogenoalkylsulphonyl and alkoxycarbonyl having in each case 1 to 4 carbon atoms in the individual alkyl or alkoxy parts and in the case of the halogenoalkyl, halogenoalkoxy and halogenoalkylsulphonyl having 1 to 5 identical or different halogen atoms, and $R^2$ represents aryl or aralkyl having 6 to 10 carbon atoms in the aryl part and in the case of the aralkyl having 1 to 4 carbon atoms in the alkyl part and in each case unsubstituted or substituted by one or more identical or different substituents, possible substituents on the aryl in each case being: halogen, nitro, cyano, alkyl and alkoxy having in each case 1 to 6 carbon atoms and halogenoalkyl, halogenoalkoxy, alkylsulphonyl, halogenoalkylsulphonyl and alkoxycarbonyl having in each case 1 to 4 carbon atoms in the individual alkyl or alkoxy parts and in the case of the halogenoalkyl, halogenoalkoxy and halogenoalkylsulphonyl having 1 to 5 identical or different halogen atoms; or represents an optionally benzo-fused hetero-aromatic 5- or 6-membered ring which contains one or more identical or different hetero atoms, such as oxygen, sulphur and nitrogen, and is unsubstituted or substituted by one or more identical or different substituents, possible substituents being halogen and alkyl having 1 to 6 carbon atoms, excluding the compound 2,5-bis-[(phenylmethyl)-sulphonyl]-1,3,4-thiadiazole.

Particularly preferred compounds of the formula (I) are those in which $R^1$ represents straight-chain or branched alkyl having 1 to 4 carbon atoms or represents phenylalkyl or naphthylalkyl which has 1 to 3 carbon atoms in the alkyl parts and is unsubstituted or substituted by one to three identical or different substituents, substituents which may be mentioned being: halogen, nitro, cyano, alkyl having 1 to 4 carbon atoms, alkoxy having 1 to 3 carbon atoms, alkylsulphonyl having 1 to 3 carbon atoms, halogenoalkyl, halogenoalkoxy and halogenoalkylsulphonyl having in each case 1 or 2 carbon atoms and 1 to 5 identical or different halogen atoms and alkoxycarbonyl having 1 or 2 carbon atoms in the alkoxy part, and $R^2$ represents phenyl, naphthyl, phenylalkyl or naphthylalkyl which has 1 or 2 carbon atoms per alkyl part and is in each case unsubstituted or substituted by one to three identical or different substituents, substituents on the rings which may be mentioned being: halogen, nitro, cyano, alkyl having 1 to 4 carbon atoms, alkoxy having 1 to 3 carbon atoms, alkylsulphonyl having 1 to 3 carbon atoms, halogenoalkyl, halogenoalkoxy and halogenoalkylsulphonyl having in each case 1 or 2 carbon atoms and 1 to 5 identical or different halogen atoms and alkoxycarbonyl having 1 or 2 carbon atoms in the alkoxy part; or represents an optionally benzo-fused hetero-aromatic 5- or 6-membered ring which contains 1, 2 or 3 identical or different hetero atoms, for example oxygen, sulphur and nitrogen, and is unsubstituted or substituted by one to three identical or different substituents. Substituents which may be mentioned for the heterocyclic radical are halogen and straight-chain or branched alkyl having 1 to 4 carbon atoms, excluding the compound 2,5-bis-[(phenylmethyl)-sulphonyl]-1,3,4-thiadiazole.

Especially preferred compounds of the formula (I) are those in which $R^1$ represents methyl, ethyl, n- or i-propyl, n-, i-, s-or t-butyl or benzyl which is unsubstituted or substituted by one to three identical or different substituents, possible substituents being: fluorine, chlorine, bromine, nitro, cyano, methyl, ethyl, t-butyl, methoxy, trifluoromethyl, trifluoromethoxy, trifluoromethylsulphonyl, methoxycarbonyl and ethoxycarbonyl, and $R^2$ represents phenyl, naphthyl, benzyl or phenethyl, in each case unsubstituted or substituted by one to three identical or different substituents, possible substituents in each case being: fluorine, chlorine, bromine, nitro, cyano, methyl, ethyl, t-butyl, methoxy, ethoxy, trifluoromethyl, trifluoromethoxy, methylsulphonyl, trifluoromethylsulphonyl, methoxycarbonyl and ethoxycarbonyl; or furthermore represents pyridyl, benzoxazolyl, benzothiazolyl, benzimidazolyl, 1,3- thiazolyl or 1,2,4-oxadiazolyl, in each case unsubstituted or substituted by one or two identical or different substituents from the group comprising fluorine, chlorine, bromine, methyl and ethyl,
excluding the compound 2,5-bis-[(phenylmethyl)-sulphonyl]-1,3,4-thiadiazole If the starting substances used are, for example, 2-methylmercapto-5-(4-chlorobenzylmercapto)-1,3,4-thiadiazole, sodium tungstate, as the catalyst, and hydrogen peroxide for the oxidation, the course of the reaction in the process according to the invention can be represented by the following equation:

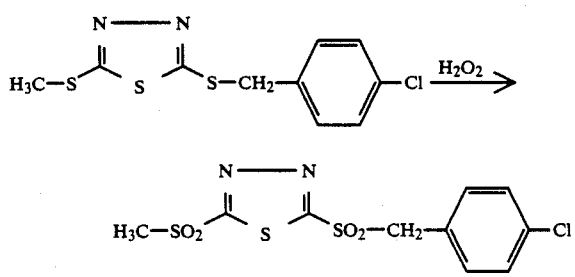

Formula (II) provides a general definition of the 2,5-dimercapto-1,3,4-thiadiazole derivatives required as starting substances for carrying out the process according to the invention. In this formula (II), $R^1$ and $R^2$ preferably or in particular represent those substituents which have been mentioned above as preferred or particularly preferred for these radicals in the description of the new 2,5-disubstituted 1,3,4-thiadiazole derivatives of the formula (I).

The 2,5-dimercapto-1,3,4-thiadiazole derivatives of the formula (II) are known in some cases and/or can be prepared by known processes in a simple analogous manner (compare, for example, European Patent Specification No. 214,732 and Japanese Patent No. 87 039,583), for example by a process in which (A) 2-substituted 1,3,4-thiadiazole derivatives of the formula (III)

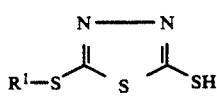 (III)

or alkali metal salts thereof
in which
$R^1$ has the abovementioned meaning,
are reacted with halides of the formula (IV)

$$X-CH_2-R^2$$ (IV)

in which
$R^2$ has the abovementioned meaning and
X represents halogen, in particular chlorine or bromine,
if appropriate in the presence of a diluent, such as, for example, acetone, methyl ethyl ketone or acetonitrile, and if appropriate in the presence of a base, such as, for example, potassium carbonate, at temperatures between 20° C. and 100° C.,
or
(B) 5-substituted 1,3,4-thiadiazoles of the formula (V)

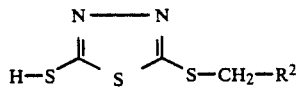 (V)

or alkali metal salts thereof,
in which
$R^2$ has the abovementioned meaning,
are reacted with halides of the formula (VI)

$$R^1-X$$ (VI)

in which
$R^1$ has the abovementioned meaning and
X represents halogen, in particular chlorine or bromine,
if appropriate in the presence of a diluent, such as, for example, acetone, methyl ethyl ketone or acetonitrile, and if appropriate in the presence of a base, such as, for example, potassium carbonate, at temperatures between 20° C. and 100° C.

The compounds of the formula (III) required as starting substances are known (compare DE-OS (German Published Specification No.) 2,459,672).

The compounds of the formula (V) required as starting substances are known (compare, for example, European Patent Specification No. 214,732, and Japanese Patent No. 87 039,583).

The halides of the formulae (IV) and (VI) also required as starting substances are generally known compounds of organic chemistry.

The oxidizing agents for the process according to the invention are known per se (compare Reaktionen der organischen Synthese (Reactions of Organic Synthesis), G. Thieme Verlag, Stuttgart (1978), page 472).

Examples which may be mentioned are hydrogen peroxide, performic acid, peracetic acid, perbenzoic acid, m-chloroperbenzoic acid and/or sodium metaperiodate, and aqueous solutions of halogen, in particular chlorine or bromine (compare S. Oae, Organic Chemistry of Sulfur, Plenum Press, N.Y., 1977, page 529 et seq.).

Preferred oxidizing agents are hydrogen peroxide and/or peracids.

The amount of oxidizing agent is in general about 1 to 4 equivalents, based on the 2,5-dimercapto-1,3,4-thiadiazole derivatives of the formula (II).

Possible diluents for the oxidation reaction are all the inert organic solvents which do not change under the oxidation conditions.

These include, preferably, chlorinated hydrocarbons, such as methylene chloride, chloroform, carbon tetrachloride, 1,2-dichloroethane, 1,2,2-trichloroethane and chlorobenzene; alcohols, preferably methanol, ethanol or isopropanol; and lower fatty acids, preferably formic acid, acetic acid or propionic acid. The process according to the invention can also be carried out in a mixture of the solvents with water or in mixtures of several solvents.

Catalysts which can be used in the oxidation are the salts, which are usually employed for this purpose, of metals of sub-groups IV, V and VI of the periodic table of the elements, and vanadium pentoxide, sodium metavanadate, sodium molybdate and/or sodium tungstate may be mentioned in particular.

The most favorable amount of oxidizing agent and catalyst for the oxidation can likewise easily be determined by preliminary experiments. The abovementioned amount of oxidizing agent is usually employed with about 0.01 to 0.1, preferably 0.015 to 0.09,mol of catalyst per mol of mercapto compound of the formula (IV). The amount of diluent is not critical and can likewise easily be determined by preliminary experiments.

The oxidation is in general carried out in the temperature range from about −60° C. to +120° C., preferably in the temperature range from −60° C. to +80° C.

The oxidation can be carried out under normal pressure or under reduced or increased pressure (for example in the pressure range from 0.5 to 1.5 bar). The oxidation is preferably carried out under normal pressure.

In the preparation of the 2,5-disubstituted 1,3,4-thiadiazole derivatives of the formula (I) according to the invention by the process according to the invention, in general in each case the equivalent amount of oxidizing agent is employed, that is to say four oxidation equivalents, and if appropriate even a greater excess, are employed per mol of 2,5-mercapto-1,3,4-thiadiazole of the formula (II).

The new 2,5-disubstituted 1,3,4-thiadiazole derivatives of the general formula (I) are isolated in the generally customary manner, for example by adding water to the reaction mixture, extracting with an organic solvent, concentrating and if appropriate recrystallizing.

The active compounds according to the invention exhibit a potent biological action and can be employed in practice for combating undesirable pests. The active compounds are suitable, for example, for use as plant protection agents, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriacea, Corynebacteriaceae and Streptomycetaceae.

Some causative organisms of fungal and bacterial diseases which come under the generic names listed above may be mentioned as examples, but not by way of limitation:

Xanthomonas species, such as, for example, *Xanthomonas campestris pv. oryzae;*

Pseudomonas species, such as, for example, *Pseudomonas syringae pv. lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, Syn: Helminthosporium);

Cochliobolus species, such as, for example, *Cochliobolus sativus* (conidia form: Drechslera, Syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alernaria species, such as, for example, *Alternaria brassicae;*

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be employed with particularly good success protectively for combating Pyricularia species on rice, Plasmopara species on vines and Venturia species on apples.

Some of the active compounds according to the invention also have a good bactericidal action and a good fungicidal action against Pellicularia species, such as, for example, Pellicularia sasakii.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutylketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionogenic and anionic emulsifiers, such as polyoxyethylene-fatty acid esters, polyoxyethylene fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and use of the active compounds according to the invention can be seen from the following examples.

PREPARATION EXAMPLES

Example 1;

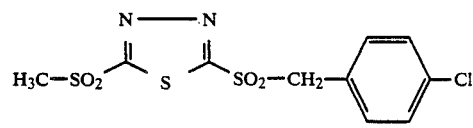

40 ml of 35% strength hydrogen peroxide solution are slowly added to 10 g (0.035 mol) of 2-methylmercapto-5-(4-chlorobenzylmercapto)-1,3,4-thiadiazole and 1 g of sodium tungstate in 100 ml of formic acid, during which the internal temperature rises to 70° C. After the dropwise addition, the reaction mixture is subsequently stirred at 70° C. for 30 minutes and then cooled to room temperature and diluted with water. The product which has precipitated is filtered off with suction and dried.

11.1 g (89.8% of theory) of 2-methylsulphonyl-5-(4-chlorobenzylsulphonyl)-1,3,4-thiadiazole are obtained as a crystalline white solid of melting point 159°–160° C.

The end products of the formula (I)

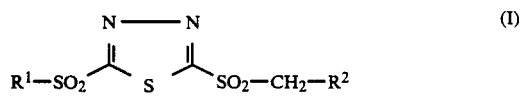

(I)

listed below in Table 1 are obtained in an analogous manner to Example 1 and taking into consideration the information in the description of the process according to the invention:

TABLE 1 - Continuation

| Example No. | R¹ | R² | Melting point (°C.) |
|---|---|---|---|
| 2 | CH₃ | (pyridyl-Cl) | 189 |
| 3 | CH₃ | (phenyl) | 138 |

TABLE 1 - Continuation-continued
| Example No. | R[1] | R[2] | Melting point (°C.) |
|---|---|---|---|
| 4 | CH$_3$ | 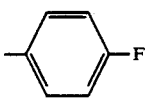 | 173 |
| 5 | CH$_3$ | 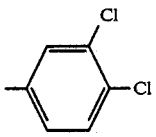 | 205-6 |
| 6 | CH$_3$ | 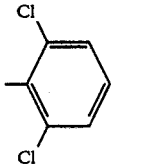 | 173 |
| 7 | CH$_3$ | 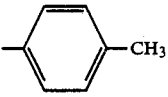 | 146 |
| 8 | CH$_3$ | 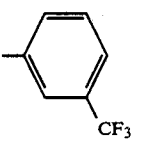 | 150 |
| 9 | CH$_3$ | 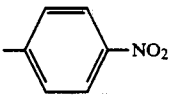 | 230-2 (decomposition) |
| 10 | CH$_3$ | 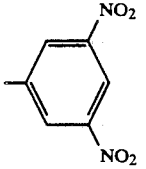 | 184-5 |
| 11 | 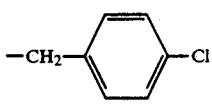 |  | 228 |
| 12 | CH$_3$ | 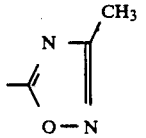 | 144-45 |
| 13 | —C(CH$_3$)$_3$ |  | 139 |
| 14 | CH$_3$ |  | 177 |

TABLE 1 - Continuation-continued
| Example No. | R¹ | R² | Melting point (°C.) |
|---|---|---|---|
| 15 | CH₃ | 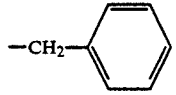 —CH₂—C₆H₅ | 105 |
| 16 | CH₃ | 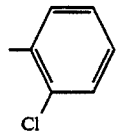 2-Cl-C₆H₄— | 150 |
| 17 | CH₃ | 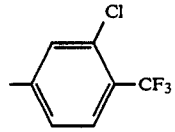 3-Cl-4-CF₃-C₆H₃— | 182–3 |
| 18 | CH₃ | 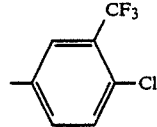 3-CF₃-4-Cl-C₆H₃— | 199–200 |
| 19 | CH₃ | 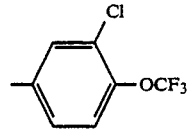 3-Cl-4-OCF₃-C₆H₃— | 181 |
| 20 | CH₃ | 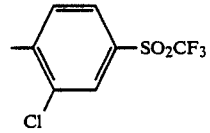 3-Cl-4-SO₂CF₃-C₆H₃— | 197 |
| 21 | CH₃ | 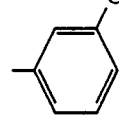 3-Cl-C₆H₄— | 152 |
| 22 | CH₃ | 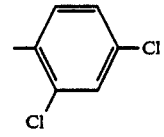 2,4-Cl₂-C₆H₃— | 178 |
| 23 | CH₃ | 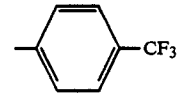 4-CF₃-C₆H₄— | 202 |
| 24 | —CH(CH₃)₂ | 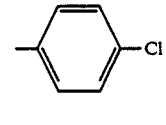 4-Cl-C₆H₄— | 143 |
| 25 | C₂H₅ |  4-Cl-C₆H₄— | 131 |

TABLE 1 - Continuation-continued

| Example No. | $R^1$ | $R^2$ | Melting point (°C.) |
|---|---|---|---|
| 26 | $CH_3$ | 1-naphthyl | 160–1 |
| 27 | $CH_3$ | $-CH_2-CH_2-C_6H_5$ | 118–9 |
| 28 | $CH_3$ | $-CH_2-C_6H_4-Cl$ (4-) | 140 |
| 29 | $CH_3$ | 2-fluorophenyl | 151 |
| 30 | $CH_3$ | 4-$OCF_3$-phenyl | 178–80 |
| 31 | $CH_3$ | $-CH_2-C_6H_4-Br$ (4-) | 185–6 |
| 32 | $-C(CH_3)_3$ | $-CH_2-C_6H_4-C(CH_3)_3$ (4-) | 196–7 |
| 33 | $CH_3$ | $-CH_2-C_6H_4-CN$ (4-) | 202–3 |
| 34 | $CH_3$ | $-CH_2-$[2,5-di-$CH_3$-4-$OCF_3$-phenyl] | 154–5 |
| 35 | $CH_3$ | 4-$OCH_3$-phenyl | 145 |
| 36 | $CH_3$ | 2-$NO_2$-phenyl | 189–90 |
| 37 | $CH_3$ | 5-methyl-2-chloro-thiazol-yl | 137 |

TABLE 1 - Continuation-continued

| Example No. | R¹ | R² | Melting point (°C.) |
|---|---|---|---|
| 38 | CH₃ | 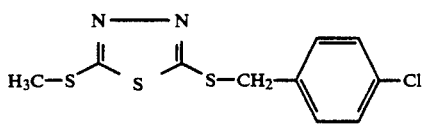 | 119-23 |

Preparation of the starting substances

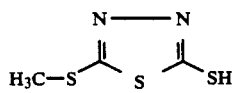

198 g (1.5 mol) of 2-methylmercapto-5-mercapto-1,3,4-thiadiazole and 240 g (1.74 mol) of potassium carbonate are heated at 40°-50° C. in 2.2 l of acetonitrile for 30 minutes. A solution of 241 g (1.5 mol) of 4-chlorobenzyl chloride in 500 ml of acetonitrile is then added dropwise at this temperature. The reaction mixture is subsequently stirred at 60°-70° C. for one hour and then filtered hot with suction and the residue is rinsed with warm acetonitrile. The reaction product crystallizes out on cooling.

389.5 g (90% of theory) of 2-methylmercapto-5-(4-chlorobenzylmercapto)-1,3,4-thiadiazole of melting point 77°-78° C. are obtained.

45.7 g =36 ml (0.6 mol) of carbon disulphide are added dropwise to a solution of 61 g (0.5 mol) of methyl dithiocarbazate in 100 ml of pyridine at 40°-50° C. and the hydrogen sulphide formed is passed into sodium hydroxide solution. When the dropwise addition has ended, the reaction mixture is heated at 100° C. for 30 minutes, the residual hydrogen sulphide is blown out with nitrogen and the solvent is distilled off. The residue is taken up in water and filtered off with suction. 71.6 g (87% of theory) of 2-methylmercapto-5-mercapto-1,3,4-thiadiazole of melting point 136° C. are obtained.

Example A

Pyricularia test (rice)/protective

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example, the substances (1), (2), (5), (6) and (8) according to the invention at an active compound concentration of 0 025% by weight in the spray liquor show a good activity.

Example B

Plasmopara test (vines)/protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20 to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, for example, the compounds (1), (3), (4), (6), (7) and (8) according to the invention exhibit a degree of action of about 90% at an active compound concentration of 10 ppm.

Example C

Venturia test (apple)/protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, for example, the compounds (1), (3), (5), (6), (7) and (8) according to the invention exhibit a degree of action of about 85% at an active compound concentration of 5 ppm It will be appreciated that the instant specification and claims are set forth by way of illustration and not limitation, and that various modifications and changes may be made without departing from the spirit and scope of the present invention.

What is claimed is:

1. A 2,5-disubstituted 1,3,4-thiadiazole of the formula

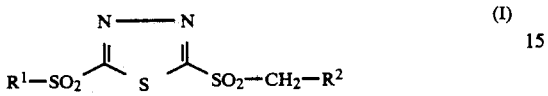

(I)

in which
R$^1$ represents straight-chain or branched alkyl having 1 to 6 carbon atoms or aralkyl which has 1 to 5 carbon atoms in the alkyl part and 6 to 10 carbon atoms in the aryl part and is unsubstituted or substituted on the aryl part by one or more identical or different substitutes selected from the group consisting of halogen, nitro, cyano, alkyl and alkoxy having in each case 1 to 6 carbon atoms and halogenoalkyl, halogenoalkoxy, alkylsulphonyl, halogenoalkylsulphonyl and alkoxycarbonyl having in each case 1 to 4 carbon atoms in the individual alkyl or alkoxy parts and in the case of the halogenoalkyl, halogenoalkoxy and halogenoalkylsulphonyl having 1 to 5 identical or different halogen atoms, and R$^2$ represents aryl or aralkyl having 6 to 10 carbon atoms in the aryl part and in the case of the aralkyl having 1 to 4 carbon atoms in the alkyl part and in each case unsubstituted or substituted on the aryl part by one or more identical or different substituents selected from the group consisting of halogen, nitro, cyano, alkyl and alkoxy having in each case 1 to 6 carbon atoms and halogenoalkyl, halogenoalkoxy, alkylsulphonyl, halogenoalkylsulphonyl and alkoxycarbonyl having in each case 1 to 4 carbon atoms in the individual alkyl or alkoxy parts and in the case of the halogenoalkyl, halogenoalkoxy and halogenoalkylsulphonyl having 1 to 5 identical or different halogen atoms; or represents a radical selected from the group consisting of pyridyl, pyrimidyl, pyridazyl, thienyl, furyl, pyrazolyl, thiadiazolyl, quinolyl, isoquinolyl, benzoxazolyl, benzothiazolyl, benzimidazolyl and 1,2,4-oxadiazolyl, which radical is unsubstituted or substituted by one or more identical or different substituents selected from the group consisting of halogen and alkyl having 1 to 6 carbon atoms, excluding the compound 2,5-bis-{(phenylmethyl)-sulphonyl}-1,3,4-thiadiazole.

2. A 2,5-disubstituted 1,3,4-thiadiazole according to claim 1, in which
R$^1$ represents straight-chain or branched alkyl having 1 to 4 carbon atoms or represents phenylalkyl or naphthylalkyl which has 1 to 3 carbon atoms in the alkyl parts and is unsubstituted or substituted by one to three identical or different substituents, selected from the group consisting of halogen, nitro, cyano, alkyl having 1 to 4 carbon atoms, alkoxy having 1 to 3 carbon atoms, alkylsulphonyl having 1 to 3 carbon atoms, halogenoalkyl, halogenoalkoxy and halogenoalkylsulphonyl having in each case 1 or 2 carbon atoms and 1 to 5 identical or different halogen atoms and alkoxycarbonyl having 1 or 2 carbon atoms in the alkoxy part, and R$^2$ represents phenyl, naphthyl, phenylalkyl or naphthylalkyl which has 1 or 2 carbon atoms per alkyl part and is in each case unsubstituted or substituted on the rings by one to three identical or different substituents selected from the group consisting of halogen, nitro, cyano, alkyl having 1 to 4 carbon atoms, alkoxy having 1 to 3 carbon atoms, alkylsulphonyl having 1 to 3 carbon atoms, halogenoalkyl, halogenoalkoxy and halogenoalkylsulphonyl having in each case 1 or 2 carbon atoms and 1 to 5 identical or different halogen atoms and alkoxycarbonyl having 1 or 2 carbon atoms in the alkoxy part; or represents a radical selected from the group consisting of pyridyl, pyrimidyl, pyridazyl, thienyl, furyl, pyrazolyl, thiadiazolyl, quinolyl, isoquinolyl, benzoxazolyl, benzothiazolyl, benzimidazolyl and 1,2,4-oxadiazolyl, which radical is unsubstituted or substituted by one to three identical or different substituents selected from the group consisting of halogen and straight-chain or branched alkyl having 1 to 4 carbon atoms, excluding the compound 2,5-bis-{(phenylmethyl)-sulphonyl}-1,3,4-thiadiazole.

3. A 2,5-disubstituted 1,3,4-thiadiazole according to claim 1, in which
R$^1$ represents methyl, ethyl, n- or i-propyl, n-, i-, s- or t-butyl or benzyl which is unsubstituted or substituted by one to three identical or different substituents, selected from the group consisting of fluorine, chlorine, bromine, nitro, cyano, methyl, ethyl, t-butyl, methoxy, trifluoromethyl, trifluoromethoxy, trifluoromethylsulphonyl, methoxycarbonyl and ethoxycarbonyl,
and
R$^2$ represents phenyl, naphthyl, benzyl or phenethyl, in each case unsubstituted or substituted by one to three identical or different substituents selected from the group consisting of fluorine, chlorine, bromine, nitro, cyano, methyl, ethyl, t-butyl, methoxy, ethoxy, trifluoromethyl, trifluoromethoxy, methylsulphonyl, trifluoromethylsulphonyl, methoxycarbonyl and ethoxycarbonyl; or furthermore represents pyridyl, benzoxazolyl, benzothiazolyl, benzimidazolyl, 1,3-thiazolyl, or 1,2,4-oxadiazolyl, in each case unsubstituted or substituted by one or two identical or different substituents selected from the group consisting of fluorine, chlorine, bromine, methyl and ethyl, excluding the compound 2,5-bis-[(phenylmethyl)-sulphonyl]-1,3,4-thiazole.

4. A compound according to claim 1, wherein such compound is 2-methylsulphonyl-5-(4-chlorobenzylsulphonyl)-1,3,4-thiadiazole of the formula

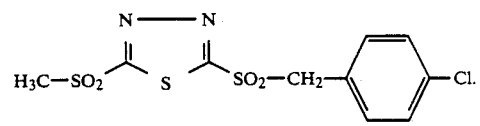

5. A compound according to claim 1, wherein such compound is 2-methylsulphonyl-5-(4-fluorobenzylsulphonyl)-1,3,4-thiadiazole of the formula

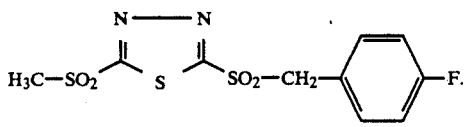

6. A compound according to claim 1, wherein such compound is 2-ethylsulphonyl-5-(4-chlorobenzylsulphonyl)-1,3,4-thiadiazole of the formula

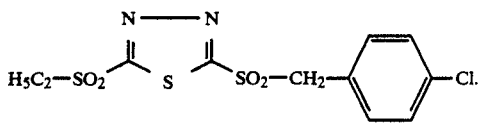

7. A compound according to claim 1, wherein such compound is 2-methylsulphonyl-5-(4-chlorophenylpropylsulphonyl)-1,3,4-thiadiazole of the formula

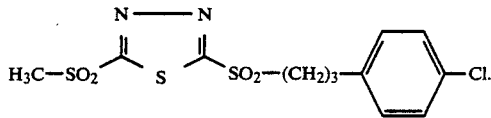

8. A compound according to claim 1, wherein such compound is 2-methylsulphonyl-5-(4-chlorophenethylsulphonyl)-1,3,4-thiadiazole of the formula

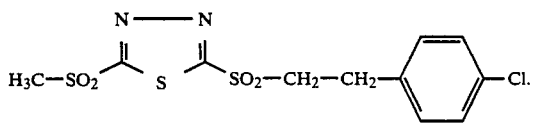

9. A fungicidal composition comprising a fungicidally effective amount of a compound according to claim 1 and a diluent.

10. A method of combating fungi which comprises applying to such fungi or to a fungus habitat a fungicidally effective amount of a compound according to claim 1.

11. The method according to claim 10, wherein such compound is
2-methylsulphonyl-5-(4-chlorobenzylsulphonyl)-1,3,4-thiadiazole,
2-methylsulphonyl-5-(4-fluorobenzylsulphonyl)-1,3,4-thiadiazole,
2-ethylsulphonyl-5-(4-chlorobenzylsulphonyl)-1,3,4-thiadiazole,
2-methylsulphonyl-5-(4-chlorophenylpropylsulphonyl)-1,3,4-thiadiazole, or
2-methylsulphonyl-5-(4-chlorophenethylsulphonyl)-1,3,4-thiadiazole.

* * * * *